United States Patent [19]
Fletcher

[11] 4,236,003
[45] Nov. 25, 1980

[54] V-TRIAZOLYL-[4,5-D]-PYRIMIDH.

[75] Inventor: Ian J. Fletcher, Magden, Switzerland

[73] Assignee: Ciba-Geigy Corporation, Ardsley, N.Y.

[21] Appl. No.: 16,769

[22] Filed: Mar. 2, 1979

Related U.S. Application Data

[62] Division of Ser. No. 846,875, Oct. 31, 1977, Pat. No. 4,157,443.

[30] Foreign Application Priority Data

Nov. 11, 1976 [LU] Luxembourg .............................. 76169
Jul. 11, 1977 [CH] Switzerland ........................... 8523/77

[51] Int. Cl.$^3$ ........................................... C07D 487/04
[52] U.S. Cl. ............................ 544/254; 252/301.25; 544/418; 544/323; 544/324
[58] Field of Search ......................................... 544/254

[56] References Cited

U.S. PATENT DOCUMENTS

| | | | |
|---|---|---|---|
| 3,819,631 | 6/1974 | Broughton et al. | 544/254 |
| 3,933,822 | 1/1976 | Broughton et al. | 544/254 |
| 4,027,025 | 3/1977 | Schaeffer et al. | 544/254 |

OTHER PUBLICATIONS

Benson et al., "J. Amer. Chem. Soc.," vol. 72, 1950, pp. 1816–1818.
Hartzel et al., "J. Amer. Chem. Soc.," vol. 76, 1954, pp. 2263–2265.
Timmis et al., "J. Pharmacy and Pharmacol," vol. 9, 1957, pp. 46–47.

*Primary Examiner*—Donald G. Daus
*Assistant Examiner*—James H. Turnipseed
*Attorney, Agent, or Firm*—Prabodh I. Almaula

[57] ABSTRACT

New v-Triazolyl-[4,5-d]-pyrimidines of the formula (1)

wherein Q and $Q_1$ independently of one another are a secondary or tertiary amino radicals and X, $X_1$ and $X_2$ are certain non-chromophoric substituents, their preparation and their use for the optical brightening of organic materials are provided.

5 Claims, No Drawings

V-TRIAZOLYL-[4,5-D]-PYRIMIDH.

This is a divisional of application Ser. No. 846,875 filed on Oct. 31, 1977, now U.S. Pat. No. 4,157,443 issued on June 5, 1979.

The present invention relates to novel v-triazolyl[4,5-d]-pyrimidines, their preparation and their use for the optical brightening of organic materials.

The novel v-triazolyl[4,5-d]-pyrimidines are of the formula

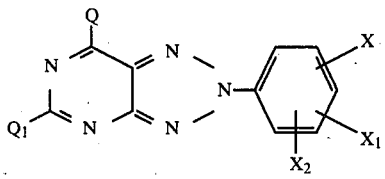
(1)

in which Q and $Q_1$ independently of one another are a secondary or tertiary amino radical, X is hydrogen, alkyl having 1 to 6 carbon atoms, alkoxy having 1 to 6 carbon atoms, allyloxy, hydroxyalkoxy having 2 to 4 carbon atoms, alkoxyalkoxy having a total of 3 to 8 carbon atoms, benzyloxy, phenethyloxy, halogen, phenoxy, phenoxyalkoxy having 1 to 3 carbon atoms in the alkoxy part, sulpho, cyano, —COOY, in which Y is hydrogen, a salt-forming cation or alkyl having 1 to 18 carbon atoms, or —$SO_2NY_1Y_2$ or —$CONY_1Y_2$, in which $Y_1$ and $Y_2$ independently of one another are hydrogen or alkyl having 1 to 4 carbon atoms, or together with $X_1$, is also the methylenedioxy or ethylenedioxy radical or the methyleneoxymethyleneoxy radical, $X_1$ is hydrogen, alkyl having 1 to 4 carbon atoms, alkoxy having 1 to 4 carbon atoms, halogen, sulpho, cyano, —COOY, in which Y is hydrogen, a salt-forming cation or alkyl having 1 to 18 carbon atoms, or —$SO_2NY_1Y_2$ or —$CONY_1Y_2$, in which $Y_1$ and $Y_2$ independently of one another are hydrogen or alkyl having 1 to 4 carbon atoms, or together with X is also the methylenedioxy or ethylenedioxy radical or the methyleneoxymethyleneoxy radical, and $X_2$ is hydrogen, alkyl having 1 to 4 carbon atoms, alkoxy having 1 to 4 carbon atoms or halogen.

Secondary and tertiary amino radicals Q and $Q_1$ are to be understood as meaning radicals which are of the formulae —$NR°R_1°$ and —$NR_2°R_3°$ respectively, in which $R°$ and $R_1°$ and, respectively, $R_2°$ and $R_3°$ independently of one another are unsubstituted alkyl having 1 to 12, and preferably 1 to 4, carbon atoms, hydroxyalkyl having 2 to 12, and preferably 2 to 6 carbon atoms, alkyl having 2 to 4 carbon atoms which is substituted by alkoxy having 1 to 8 carbon atoms or dialkylamino having 2 to 4 carbon atoms per alkyl part, or together with the nitrogen atoms are a 5-membered or 6-membered saturated heterocyclic structure which can contain other hetero-atoms, and $R°$ and $R_2°$ are also hydrogen.

Possible heterocyclic structures are, for example, pyrrolidine, piperidine, piperazine and morpholine, which can be unsubstituted or substituted by alkyl having 1 to 4 carbon atoms or halogen. Piperazine rings can be substituted in the 4-position by alkyl or hydroxyalkyl having 1 to 4 carbon atoms or can also be quaternised.

Sulpho is to be understood as meaning, in each case, the radical —$SO_3M$, in which M is hydrogen or a salt-forming cation. Possible cations are, in general, those of alkaline earth metals, for example of calcium, barium or magnesium, and also especially of alkali metals, for example of sodium or potassium.

Important compounds within the scope of the compounds of the formula (1) are those of the formulae

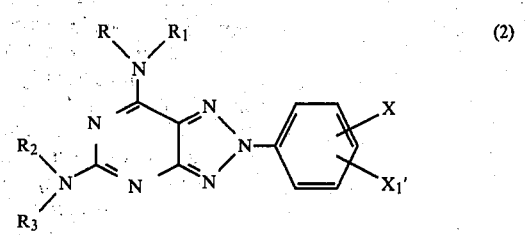
(2)

in which R and $R_2$ independently of one another are hydrogen, alkyl having 1 to 12 carbon atoms, hydroxyalkyl having 2 to 6 carbon atoms or dialkylaminoalkyl having 2 to 4 carbon atoms per alkyl part, or R together with $R_1$, or $R_2$ together with $R_3$, are the complement to a 5-membered or 6-membered saturated heterocyclic structure, which can contain yet further hetero-atoms, $R_1$ and $R_3$ independently of one another are alkyl having 1 to 12 carbon atoms or hydroxyalkyl having 2 to 6 carbon atoms, or $R_1$ together with R, or $R_3$ together with $R_2$, are the complement to a 5-membered or 6-membered saturated heterocyclic structure, which can contain yet further hetero-atoms, X is hydrogen, alkyl having 1 to 6 carbon atoms, alkoxy having 1 to 6 carbon atoms, allyloxy, hydroxyalkoxy having 2 to 4 carbon atoms, alkoxyalkoxy having a total of 3 to 8 atoms, benzyloxy, phenethoxy, halogen, phenoxy, phenoxyalkoxy having 1 to 3 carbon atoms in the alkoxy part, sulpho, cyano, —COOY, in which Y is hydrogen, a salt-forming cation or alkyl having 1 to 18 carbon atoms, or —$SO_2NY_1Y_2$ or —$CONY_1Y_2$, in which $Y_1$ and $Y_2$ independently of one another are hydrogen or alkyl having 1 to 4 carbon atoms, or together with $X_1'$ is also the methylenedioxy or ethylenedioxy radical or the methyleneoxymethyleneoxy radical, and $X_1'$ is hydrogen, alkyl having 1 to 4 carbon atoms, alkoxy having 1 to 4 carbon atoms, halogen, sulpho, cyano, —COOY, in which Y is hydrogen, a salt-forming cation or alkyl having 1 to 4 carbon atoms, or together with X is also the methylenedioxy or ethylenedioxy radical or the methyleneoxymethyleneoxy radical, and

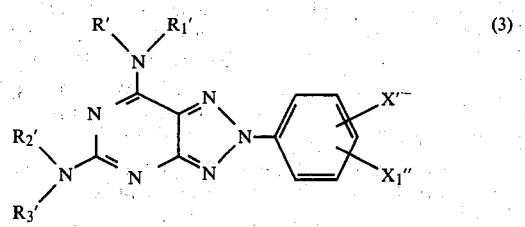
(3)

in which $R'$ and $R_2'$ independently of one another are hydrogen, alkyl having 1 to 4 carbon atoms or hydroxyalkyl having 2 to 6 carbon atoms, or $R'$ together with $R_1'$, or $R_2'$ together with $R_3'$, are the complement to a 5-membered or 6-membered saturated heterocyclic structure which can contain a further oxygen or nitrogen atom, $R_1'$ and $R_3'$ independently of one another are alkyl having 1 to 4 carbon atoms or hydroxyalkyl having 2 to 6 carbon atoms, or $R_1'$ together with $R'$, or $R_3'$ together with $R_2'$, are the complement to a 5-membered or 6-membered saturated heterocyclic structure which can contain a further oxygen or nitrogen atom, X' is hydrogen, alkyl having 1 to 4 carbon atoms, alkoxy having 1 to 4 carbon atoms, allyloxy, hydroxyalkoxy having 2 to 4 carbon atoms, alkoxy-alkoxy having a total of 3 to 8 carbon atoms, benzyloxy, phenethoxy, chlorine, phenoxy, phenoxypropoxy, sulpho, cyano, —COOY, in which Y is hydrogen, a salt-forming cation or alkyl having 1 to 18 carbon atoms, or —SO$_2$NY$_1$Y$_2$ or —CONY$_1$Y$_2$, in which Y$_1$ and Y$_2$ independently of one another are hydrogen or alkyl having 1 to 4 carbon atoms, or together with X$_1$" is also the methylenedioxy or ethylenedioxy radical or the methyleneoxymethyleneoxy radical, and X$_1$" is hydrogen, alkyl having 1 to 4 carbon atoms, alkoxy having 1 to 4 carbon atoms or chlorine, or together with X' is also the methylenedioxy or ethylenedioxy radical or the methyleneoxymethyleneoxy radical.

Compounds of interest are v-triazolyl[4,5-d]-pyrimidines of the formula

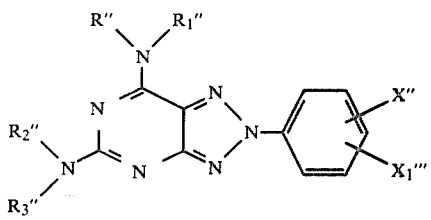

(4)

in which R" and R$_2$" independently of one another are hydrogen, alkyl having 1 to 4 carbon atoms or hydroxyethyl, or R" together with R$_1$", or R$_2$" together with R$_3$", are pyrrolidino, piperidino, morpholino, N'-hydroxyethylpiperazino or N'-hydroxyethylpiperazino quaternised by alkyl having 1 to 4 carbon atoms, R$_1$" and R$_3$" independently of one another are alkyl having 1 to 4 carbon atoms or hydroxyethyl, or R$_1$" together with R", or R$_3$" together with R$_2$", are pyrrolidino, piperidino, morpholino, N'-hydroxyethylpiperazino or N'-hydroxyethylpiperazino quaternised by alkyl having 1 to 4 carbon atoms, and X" is hydrogen, methyl, chlorine, alkoxy having 1 to 4 carbon atoms, allyloxy, hydroxyalkoxy having 2 to 4 carbon atoms, alkoxyalkoxy having 3 to 6 carbon atoms, benzyloxy, phenoxy, phenoxypropoxy, sulpho, cyano, —COOY, in which Y is hydrogen, a salt-forming cation or alkyl having 1 to 4 carbon atoms, or —SO$_2$NY$_1$Y$_2$ or —CONY$_1$Y$_2$, in which Y$_1$ and Y$_2$ independently of one another are hydrogen or alkyl having 1 to 4 carbon atoms, or X" and X$_1$'" together are 3,4-methylenedioxy or 3,4-ethylenedioxy or 3,4-methyleneoxymethyleneoxy, and X$_1$'" is hydrogen, alkyl having 1 to 4 carbon atoms, alkoxy having 1 to 4 carbon atoms or chlorine.

Compounds of particular importance are v-triazolyl[4,5-d]-pyrimidines of the formula

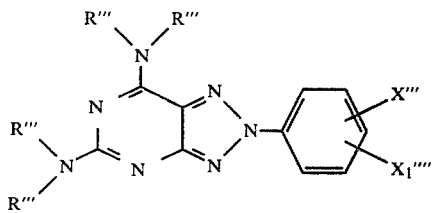

(5)

in which R'" is alkyl having 1 to 4 carbon atoms or, together with the nitrogen atom, is piperidino or morpholino, X'" is hydrogen, methyl, allyloxy, hydroxyethoxy, alkoxyalkoxy having a total of 3 to 6 carbon atoms, benzyloxy, alkoxy having 1 to 4 carbon atoms, phenoxy, phenoxypropoxy or sulpho, or together with X$_1$"" is 3,4-methylenedioxy or 3,4-ethylenedioxy or 3,4-methyleneoxymethyleneoxy, and X$_1$"" is hydrogen, alkyl having 1 to 4 carbon atoms or methoxy, or together with X'" is 3,4-methylenedioxy or 3,4-ethylenedioxy or 3,4-methyleneoxymethyleneoxy.

The v-triazolyl[4,5-d]pyrimidines of the formula (1) can be prepared by processes which are known per se. They can be obtained, for example, when an amine of the formula

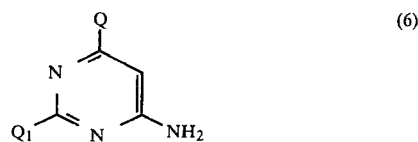

(6)

in which Q and Q$_1$ are as defined above, is coupled with a diazonium salt of the formula

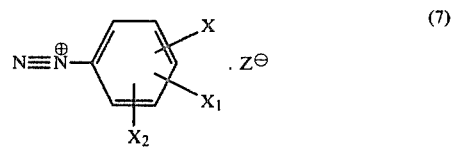

(7)

in which Z is an anion and X, X$_1$ and X$_2$ are as defined above, and the resulting o-aminoazo compound of the formula

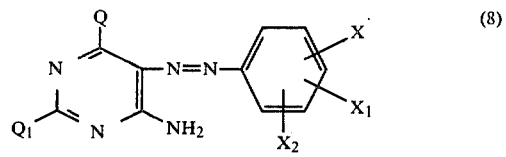

(8)

in which Q, Q$_1$ and X to X$_2$ are as defined above, is subjected to an oxidative cyclisation which is known per se (c.f., for example, U.S. Pat. No. 2,543,333).

Possible anions Z are, for example, as halogen ion, such as a chloride or bromide ion, a sulphate ion or a fluoborate ion.

Some of the amines in which X is a radical bonded via an oxygen atom to the benzene ring, which are required for the preparation of the diazonium salts of the formula (7), are known and some are novel. The novel amines can be prepared by known methods, for example by reacting p-nitrochlorobenzene with an alcohol and subsequently reducing the nitro group to the amino group. Suitable amines of this type are, for example, 1-methoxy-2-(4-aminophenoxy)-ethane, 1-isopropoxy-2-(4-aminophenoxy)-ethane, 1-n-butoxy-2-(4-aminophenoxy)-ethane, 1-methoxy-2-(4-aminophenoxy)-isopropane, 1-hydroxy-2-(4-aminophenoxy)-ethane or 2-methoxy-4-(4-aminophenoxy)-sec.-butane.

Oxidising agents which can be used are very diverse, thus, for example, chromic acid, alkali metal bichromates, hydrogen peroxide, lead tetraacetate, potassium ferricyanide, ferric chloride and copper-II sulphate. In acid solvents, for example aqueous acetic acid, alkali metal bichromates, hydrogen peroxide or lead tetraacetate are preferably used and in basic solvents, for example a pyridine/water mixture, potassium ferricyanide is preferably used. The oxidative cyclisation is preferably effected with copper-II sulfate in a pyridine/water mixture. The oxidation with copper-II salts, such as copper-II sulphate or copper-II chloride, can advantageously also be carried out in methanol or methanol/water mixtures in the presence of ammonium salts or amine salts, such as monoalkanolamines or dialkanolamines. The coupling of a compound of the formula (5) with a compound of the formula (6) is carried out at a temperature of −10 to 20° C., preferably of 0° to 10° C. The oxidative cyclisation is effected at a temperature of 70° to 100° C., preferably 90° to 100° C.

In the dissolved or finely divided state, the novel compounds defined above have a more or less pronounced fluorescence. They can be used for the optical brightening of very diverse synthetic, semi-synthetic or natural organic materials or or substances which contain such organic materials.

The following groups of organic materials, where optical brightening thereof is relevant, may be mentioned as examples of the above, without the survey given below being intended to express any restriction thereto:

I. Synthetic organic high-molecular materials
  (a) polymerisation products based on organic compounds which contain at least one polymerisable carbon-carbon double bond, i.e. the homopolymers or copolymers thereof and also the after-treatment products thereof, for example, crosslinking products, grafting products of degradation products, polymer blends or products obtained by modifying reactive groups, for example polymers based on α,β-unsaturated carboxylic acids or derivatives of such carboxylic acids, and especially on acrylic compounds (for example acrylates, acrylic acid, acrylonitrile, acrylamides and the derivatives thereof or the methacrylic analogues thereof) and on olefine hydrocarbons (for example ethylene, propylene, styrenes or dienes, and also so-called ABS polymers), and polymers based on vinyl and vinylidene compounds (for example vinyl chloride, vinyl alcohol and vinylidene chloride).
  (b) polymerisation products which are obtainable by ring opening, for example polyamides of the polycaprolactam type, and also polymers which are obtainable by polyaddition or by polycondensation, such as polyethers or polyacetals,
  (c) polycondensation products or precondensates based on bifunctional or polyfunctional compounds having groups capable of undergoing a condensation reaction, the homocondensation and cocondensation products thereof and also after-treatment products, for example polyesters, especially saturated (for example ethylene glycol terephthalic acid polyesters) or unsaturated (for example maleic acid/dialcohol polycondensates and also their crosslinking products with copolymerisable vinyl monomers), non-branched and branched (also those based on polyhydric alcohols, for example alkyd resins) polyesters, polyamides (for example hexamethylenediamine adipate), maleate resins, melamine resins, their precondensates and analogues, polycarbonates and silicones, and
  (d) polyaddition products such as polyurethanes (crosslinked and non-crosslinked) and epoxide resins.

II. Semi-synthetic organic materials, for example cellulose esters of various degrees of esterification (so-called 2½-acetate and triacetate) or cellulose ethers, regenerated cellulose (viscose or cuprammonium cellulose), or their after-treatment products, and casein plastics.

III. Natural organic materials of animal or vegetable origin, for example those based on cellulose or proteins, such as cotton, wool, linen, silk, natural lacquer resins, starch and casein.

The organic materials to be optically brightened can be in very diverse states of processing (raw materials, semi-finished goods or finished goods). On the other hand, they can be in the form of structures of very diverse shapes, i.e., for example, in the form of predominantly three-dimensional bodies, such as slabs, profiles, injection mouldings, various machined articles, chips, granules or foams, and also in the form of predominantly two-dimensional bodies, such as films, sheets, lacquers, coverings, impregnations and coatings, or in the form of predominantly one-dimensional bodies such as filaments, fibres, flocks and wires. The said materials can, on the other hand, also be in an unshaped state, in very diverse homogeneous or inhomogeneous forms of division, for example in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings or flocked structures or in the form of woven textile fabrics or textile laminates and knitted fabrics, and also in the form of papers, cardboards or paper pulps.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, nonwovens, flocked substrates or laminates, are to be optically brightened according to the invention, this is advantageously effected in an aqueous medium, in which the compounds in question are present in a finely divided form (suspensions, so-called microdispersions or possibly solutions). If desired, dispersing agents, stabliisers, wetting agents and further auxiliaries can be added during the treatment.

Depending on the type of brightener compound used, it can prove advantageous to carry out the treatment in a neutral or alkaline or acid bath. The treatment is usually carried out at temperatures of about 20° to 140° C., for example at the boiling point of the bath or near it (about 90° C.). Solutions or emulsions in organic solvents can also be used for the finishing, according to the invention, of textile substrates, as is practised in the dyeing trade in so-called solvent dyes (pad-thermofix application, or exhaustion dye processes in dyeing machines).

The novel optical brighteners according to the present invention can furthermore be added to, or incorporated in, the materials before or during their shaping. Thus they can, for example, be added to the compression moulding compositions or injection moulding compositions during the production of films, sheets (for example hot milling into polyvinyl chloride) or mouldings.

Where fully synthetic or semi-synthetic organic materials are being shaped by spinning processes or via spinning compositions, the optical brighteners can be applied in accordance with the following processes:
  addition to the starting substances (for example monomers) or intermediates (for example precondensates or prepolymers), i.e. before or during the polymerisation, polycondensation or polyaddition, powdering onto polymer chips or granules for spinning compositions, bath dyeing of polymer chips or granules for spinning compositions, metered addition to spinning melts or spinning solutions, and application to the tow before stretching.

The novel optical brighteners according to the present invention can, for example, also be employed in the following use forms:

(a) mixed with dyes (shading) or pigments (coloured pigments or especially, for example, white pigments), or as an additive to dye baths, printing pastes, discharge pastes or reserve pastes, and also for the after-treatment of dyeings, prints or discharge prints, (b) mixed with so-called "carriers", wetting agents, plasticisers, swelling agents, anti-oxidants, light stabilisers, heat stabilisers and chemical bleaching agents (chlorite bleach or bleaching bath additives), (c) mixed with crosslinking agents or finishing agents (for example starch or synthetic finishes) and in combination with the most diverse textile finishing processes, especially synthetic resin finishes (for example creaseproof finishes such as "wash-and-wear", "permanent-press" or "no-iron"), and also flameproof finishes, soft handle finishes, anti-soiling finishes or antistatic finishes, or anti-microbial finishes, (d) incorporation of the optical brighteners into polymeric carriers (polymerisation, polycondensation or poly-addition products), in a dissolved or dispersed form, for use, for example, in coating agents, impregnating agents or binders (solutions, dispersions and emulsions) for textiles, fleeces, paper and leather, (e) as additives to so-called "master batches", (f) as additives to the most diverse industrial products in order to render these more marketable (for example improving the appearance of soaps, washing agents and pigments), (g) in combination with other optically brightening substances, (h) in spinning bath formulations, i.e. as additives to spinning baths, such as are used for improving the slip for the further processing of synthetic fibres, or from a special bath before stretching the fibre, (i) as scintillators for various purposes of a photographic nature, for example for elecrophotographic reproduction or supersensitisation, and (j) depending on the substitution, as laser dyes.

If the brightening process is combined with textile treatment methods or finishing methods, the combined treatment can in many cases advantageously be carried out with the aid of appropriate stable formulations which contain the optically brightening compounds in such concentration that the desired brightening effect is achieved.

In certain cases, the brighteners are made fully effective by an after-treatment. This can, for example, be a chemical treatment (for example acid treatment), a thermal treatment (for example heat) or a combined chemical/thermal treatment. Thus, for example, the appropriate procedure to follow in optically brightening a range of fibre substrates, for example polyester fibres, with the brighteners according to the invention is to impregnate these fibres with the aqueous dispersions (or where appropriate also solutions) of the brighteners at temperatures below 75° C., for example at room temperature, and to subject them to a dry heat treatment at temperatures above 100° C., it generally being advisable additionally to dry the fibre material beforehand at a moderately elevated temperature, for example at not less than 60° C. and up to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or be combined in a single operation.

The amount of the novel optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and in some cases of up to about 2 percent by weight can also be employed. For most practical purposes, amounts between 0.0005 and 0.5 percent by weight are of preferred interest.

For various reasons it is frequently appropriate to employ the brighteners not in the form of the compounds themselves, i.e. as the pure compounds, but as a mixture with very diverse auxiliaries and diluents, for example anhydrous sodium sulphate, sodium sulphate decahydrate, sodium chloride, sodium carbonate, alkali metal phosphates, such as sodium orthophosphate or potassium orthophosphate, sodium pyrophosphate or potassium pyrophosphate and sodium tripolyphosphates and potassium tripolyphosphates, or alkali metal silicates.

The novel optical brighteners are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents at any stage of the production process of the washing agent, for example to the so-called "slurry" before spray-drying, to the washing powder, or during the preparation of liquid washing agent combinations. They can be added either in the form of a solution or dispersion in water or other solvents or, without auxiliaries, as a dry brightener powder. For example, the brighteners can be mixed, kneaded or ground with the detergent substances and, in this form, mixed into the finished washing powder. They can, however, also be sprayed in a dissolved or predispersed form onto the finished washing agent.

Possible washing agents are the known mixtures of detergent substances, for example soap in the form of chips and powders, synthetics, soluble salts of sulphonic acid half-esters of higher fatty alcohols, arylsulphonic acids having higher and/or multiple alkyl substituents, sulphocarboxylic acid esters of medium to higher alcohols, fatty acid acylamino-alkyl- or acylaminoarylglycerolsulphonates, phosphoric acid esters of fatty alcohols and the like. Examples of so-called "builders" which can be used are alkali metal polyphosphates and polymetaphosphates, alkali metal pyrophosphates, alkali metal salts of carboxymethylcelullose and other "soil redeposition inhibitors", and also alkali metal silicates, alkali metal carbonates, alkali metal borates, alkali metal perborates, nitrilotriacetic acid, ethylenediaminetetraacetic acid and foam stabilisers, such as alkanolamides of higher fatty acids. The washing agents can also contain, for example: antistatic agents, superfatting skin protection agents, such as lanolin, enzymes, antimicrobial agents, perfumes and dyes.

The novel optical brighteners have the particular advantage that they are also effective in the presence of active chlorine donors, for example hypochlorite, and can be used without significant loss of effect in wash liquors containing non-ionic washing agents, for example alkylphenol polyglycol ethers.

The compounds according to the invention are added in amounts of 0.005–1% or more, relative to the weight of the liquid or pulverulent, finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

The washing treatment is carried out, for example, as follows:

The cited textiles are treated for 1 to 30 minutes at 20° to 100° C. in a wash liquor which contains 1 to 10 g/kg of a composite washing agent containing a builder and 0.05 to 1%, relative to the weight of the washing agent, of the brighteners claimed. The liquor ratio can be 1:3 to 1:50. After washing, rinsing and drying are carried out as usual. The wash liquor can contain 0.2 g/l of active chlorine (for example in the form of hypochlorite) or 0.1 to 2 g/l of sodium perborate, as a bleaching additive.

In the examples, percentages are always percentages by weight. Unless otherwise stated, the melting points and boiling points are uncorrected.

EXAMPLE 1

5.9 g of p-toluidine are dissolved in 140 ml of water and 16.5 ml of concentrated hydrochloric acid, with stirring, the solution is cooled to 0° to 5° C. and a solution of 3.8 g of sodium nitrite in 10 ml of water is added in the course of 15 to 20 minutes at this temperature. The solution is then stirred for a further 30 minutes at 0° to 5° C. and added dropwise, at 0° to 5° C., to a solution, which has been pre-cooled to 0° C., of 10.0 g of 4-amino-2,6-bis-(dimethylamino)-pyrimidine in 100 ml of pyridine, whereupon an exothermic reaction takes place and a yellow suspension forms. After all of the solution has run in, the resulting suspension is left to stand for 6 hours at 0° to 5° C. and is then stirred for 12 hours at 20° C. The product formed is filtered off, washed with water and dried in vacuo at 70° C. This gives 16.3 g (99% of theory) of the yellow azo material having a melting point of 172° to 174° C.

15.0 g of the resulting compound are dissolved in 125 ml of pyridine at 60° C., with stirring, and a solution of 31.3 g of copper-II sulphate pentahydrate in 125 ml of water is added at this temperature. The mixture is then stirred under reflux for 4 hours and cooled to 20° C. and the product is filtered off, washed well with water and dried in vacuo at 100° C. Recrystallisation from chlorobenzene while treating with bleaching earth gives 10.7 g (72% of theory) of the compound of the formula

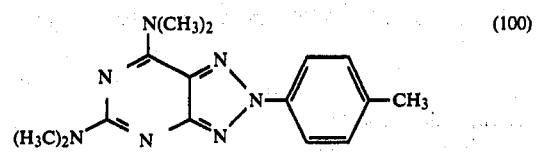

(100)

in the form of pale yellow crystals. Melting point: 209° to 210° C.

The compounds of the formula

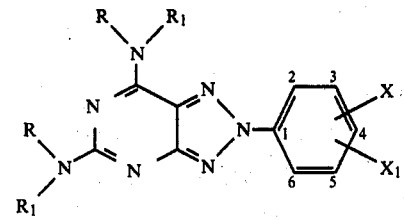

which are listed in Table I can be prepared in a manner similar to that described above using the corresponding 4-amino-2,6-diamono-pyrimidines and substituted anilines.

TABLE

| No. | R | $R_1$ | X | $X_1$ | Melting point uncorrected in °C. |
|---|---|---|---|---|---|
| (101) | $CH_3$ | $CH_3$ | 4-$OCH_3$ | H | 209–210 |
| (102) | $CH_3$ | $CH_3$ | 4-Cl | H | 270–272 |
| (103) | $CH_3$ | $CH_3$ | 3-Cl | H | 198–199 |
| (104) | $CH_3$ | $CH_3$ | H | H | 199–201 |
| (105) | $CH_3$ | $CH_3$ | 3-$CH_3$ | H | 163–164 |
| (106) | $CH_3$ | $CH_3$ | 2-$CH_3$ | H | 150–151 |
| (107) | $CH_3$ | $CH_3$ | 3-$OCH_3$ | H | 177.5–179 |
| (108) | $CH_3$ | $CH_3$ | 2-$OCH_3$ | H | 188–189.5 |
| (109) | $CH_3$ | $CH_3$ | 4-$O(CH_2)_3O$—⌬ | H | 135–137 |
| (110) | $CH_3$ | $CH_3$ | 4-O—⌬ | H | 216–217 |
| (111) | $CH_3$ | $CH_3$ | 4-$O(CH_2)_3CH_3$ | H | 173–174 |
| (112) | $CH_3$ | $CH_3$ | 4-$OC(CH_3)_3$ | H | 143.5–144.5 |
| (113) | $CH_3$ | $CH_3$ | 4-$SO_3Na$ | H | >350 |
| (114) | ⟨O⟩ | | H | H | 260–261 |
| (115) | ⟨O⟩ | | 4-$CH_3$ | H | 268.5–270 |
| (116) | ⟨O⟩ | | 4-$OCH_3$ | H | 245–247 |
| (117) | ⟨O⟩ | | 4-O—⌬ | H | 209–211 |
| (118) | ⟨O⟩ | | 4-$O(CH_2)_3CH_3$ | H | 222–225 |
| (119) | ⟨O⟩ | | 4-$OC(CH_3)_3$ | H | 203–205 |
| (120) | $CH_3$ | $CH_3$ | 4-$SO_2CH_3$ | H | 259–261 |
| (121) | $CH_3$ | $CH_3$ | 4-$SO_2NH_2$ | H | 315–317 |

TABLE-continued

| No. | R | R₁ | X | X₁ | Melting point uncorrected in °C |
|---|---|---|---|---|---|
| (122) | CH₃ | CH₃ | 3-SO₃Na | H | >350 |
| (123) | CH₃ | CH₃ | 2-SO₃Na | H | >350 |
| (124) | piperidino | | 4-CH₃ | H | 233–236 |
| (125) | piperidino | | 4-OCH₃ | H | 236–237,5 |
| (126) | CH₃ | CH₃ | 3-CH₃ | 5-CH₃ | 210–212 |
| (127) | CH₃ | CH₃ | 3-CH₃ | 4-CH₃ | 204–206 |
| (128) | CH₃ | CH₃ | 3-OCH₃ | 4-OCH₃ | 212–213 |
| (129) | CH₃ | CH₃ | 3,4-methylenedioxy (O-CH₂-O) | | 223,5–225 |
| (130) | CH₃ | CH₃ | 3-OCH₃ | 4-C₄H₉ | 135,5–136,5 |
| (131) | CH₃ | CH₃ | 3-CH₃ | 4-OCH₃ | 207–208 |
| (132) | CH₃ | CH₃ | 3-Cl | 4-Cl | 272–273 |
| (133) | CH₃ | CH₃ | 2-Cl | 5-Cl | 209–211 |
| (134) | C₂H₅ | C₂H₅ | 4-OCH₃ | H | 116–117 |
| (135) | C₄H₉ | C₄H₉ | 4-OCH₃ | H | 101–102 |
| (136) | CH₃ | CH₃ | 3-SO₃Na | 4-CH₃ | >350 |
| (137) | morpholino | | 3-SO₃Na | 4-CH₃ | >350 |
| (138) | CH₃ | CH₃ | 3-SO₃Na | 4-OCH₃ | >350 |
| (139) | morpholino | | 3-SO₃Na | 4-OCH₃ | >350 |
| (140) | CH₃ | CH₃ | 3-OC₂H₅ | H | 160–161 |
| (141) | CH₃ | CH₃ | 4-OC₂H₅ | H | 212–213 |
| (142) | CH₃ | CH₃ | 4-OC₂H₄OC₂H₅ | H | 154–155 |
| (143) | CH₃ | CH₃ | 4-OC₃H₇ | H | 175–176 |
| (144) | CH₃ | CH₃ | 4-OCH(CH₃)₂ | H | 162–168 |
| (145) | CH₃ | CH₃ | 4-C₂H₅ | H | 176–177 |
| (146) | CH₃ | CH₃ | 4-C₄H₉ | H | 110–112 |
| (147) | CH₃ | CH₃ | 4-OC₂H₄OC₃H₇ | H | 118–120 |
| (148) | CH₃ | CH₃ | 3-C₂H₅ | H | 117–118 |
| (149) | CH₃ | CH₃ | 4-CH(CH₃)₂ | H | 154–156 |
| (150) | CH₃ | CH₃ | 3,4-methylenedioxy | | 229–231 |
| (151) | CH₃ | CH₃ | 4-OCH₂CH=CH₂ | H | 174–175 |
| (152) | CH₃ | CH₃ | 4-OCH₂CH₂OH | H | 223–224 |
| (153) | CH₃ | CH₃ | 4-O—iso-C₄H₉ | H | 177–178 |
| (154) | CH₃ | CH₃ | 4-O—sek-C₄H₉ | H | 125–127 |
| (155) | CH₃ | CH₃ | 4-OC₂H₄OCH₃ | H | 176–177 |
| (156) | CH₃ | CH₃ | 4-OC₂H₄OCH(CH₃)₂ | H | 154–155 |
| (157) | CH₃ | CH₃ | 4-OC₂H₄O—n-C₄H₉ | H | 106–107 |
| (158) | CH₃ | CH₃ | 4-OCH(CH₃)(CH₂OCH₃) | H | 141–142 |
| (159) | CH₃ | CH₃ | 4-OC₂H₄CH(CH₃)(OCH₃) | H | 143–145 |
| (160) | CH₃ | CH₃ | 4-OC₃H₆OH | H | |
| (161) | CH₃ | CH₃ | 4-OC₄H₈OH | H | |
| (162) | CH₃ | CH₃ | 4-OCH₂—C₆H₅ | H | 179–180 |
| (163) | CH₃ | CH₃ | 4-OC₂H₄—C₆H₅ | H | |
| (164) | CH₃ | CH₃ | 3,4-(OCH₂OCH₂) | | 237–239 |

4-Amino-2,6-bis-(piperidino)-pyrimidine, which is required for the preparation of compounds (124) and (125), is prepared as follows:

32.8 g of 4-amino-2,6-dichloropyrimidine are dissolved in 200 ml of piperidine, while stirring well, and the temperature rises up to 100° C. After the reaction has subsided, the mixture is refluxed for 12 hours. The mixture containing the piperidine hydrochloride which has precipitated is poured into water. The oily product which separates out is extracted with methylene chloride, the solution is dried over magnesium sulphate and the methylene chloride is evaporated. The residue is dissolved in ether and the solution is saturated with gaseous hydrogen chloride, while stirring well and with cooling. The pale beige hydrochloride which has precipitated is filtered off and dried at 20° C. After recrystallisation from isopropanol with the addition of animal charcoal, 34.4 g (58% of theory) of 4-amino-2,6-bis-(piperidino)-pyrimidine hydrochloride with a melting point of 269° to 273° C. are obtained.

4-Amino-2,6-bis-(diethylamino)-pyrimidine, which is required for the preparation of compound (134) is prepared as follows:

10.0 g of 4-amino-2,6-dichloropyrimidine are heated with 40 ml of diethylamine for 8 hours in an autoclave at 200° C. After cooling to room temperature, the reaction mixture is poured into 200 ml of 10% strength sodium hydroxide solution and the oil which has precipitated is extracted with ether. After drying and filtering the ether solution, the latter is evaporated and the residue is distilled under a high vacuum and this gives 9.4 g (66% of theory) of 4-amino-2,6-bis-(diethylamino)-pyrimidine with a boiling point of 132° to 137° C./0.07 mm Hg.

If the diethylamine employed in the above example is replaced by di-n-butylamine, this gives 4-amino-2,6-bis-(di-n-butylamino)-pyrimidine, which is required for the preparation of compond (135) and has a boiling point of 160° to 170° C./0.05 mm Hg.

1-Ethoxy-2-(4-aminophenoxy)-ethane of the formula

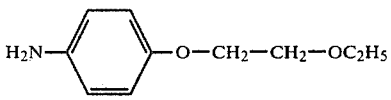

which is required for the preparation of compound (142), is prepared as follows:

157.6 g of 1-chlor-4-nitrobenzene and 108.1 g of ethylene glycol monoethyl ether are dissolved in 300 ml of dimethylsulphoxide, and 123.42 g of a 50% strength aqueous solution of potassium hydroxide are added in the course of 30 minutes, with slight cooling with ice-water. The reaction is weakly exothermic and after the cooling medium has been removed the temperature rises to about 45° C. The mixture is then heated to 65° to 70° C. and stirred overnight at this temperature. The reaction mixture is then allowed to run into a mixture of 3 liters of water and ice, while stirring well. The product which has precipitated is stirred ice-cold for a further 15 minutes and is then filtered off, washed with water and dried in vacuo. The yield of 1-ethoxy-2-(4-nitrophenoxy)-ethane is 179 g (85% of theory). Melting point=67° to 68° C.

1-Ethoxy-2-(4-nitrophenoxy)-ethane is reduced to 1-ethoxy-2-(4-aminophenoxy)-ethane with Raney nickel by the conventional route.

The amine is a pale yellow oil. Boiling point$_{0.05\ mm}$ 110° C.

EXAMPLE 2

1 g of the brightener of the formula (100) is dissolved in 1,000 ml of dimethylformamide. 100 ml of water which contain 0.06 g of an alkyl polyglycol ether are added to 3 ml of this solution. Polyamide fabric (polyamide 6 to 66) weighing 3 g is added to this brightener solution, which has been warmed to 60° C. The temperature is raised to 95° to 97° C. in the course of 10 to 15 minutes and this temperature is maintained for 30 minutes. The fabric is then rinsed in running cold water for 2 minutes and then dried for 20 minutes at 60° C.

The fabric treated in this way shows a strong brightening effect with good fastness to light.

EXAMPLE 3

1 g of the brightener of the formula (100) is dissolved in 1,000 ml of dimethylformamide. 100 ml of water which contain 0.12 ml of 85% strength formic acid are added to 3 ml of this solution. Polyamide fabric (polyamide 6 or 66) weighing 3 g is added to this brightener solution, which has been warmed to 60° C. The temperature is raised to 95° to 97° C. in the course of 10 to 15 minutes and this temperature is maintained for 30 minutes. The fabric is then rinsed in running cold water for 2 minutes and subsequently is dried for 20 minutes at 60° C.

The fabric treated in this way shows a strong brightening effect with good fastness to light.

EXAMPLE 4

Using a liquor ratio of 1:20, polyamide fiber fabric (for example "Perlon-Helanca") is washed for 15 minutes in a liquor, at 55° C., which contains, per liter, 0.002 g of a brightener of the formula (100) and 4 g of a washing agent of the following composition: 15.7% of an alkyl arylsulphonate, 3.7% of a fatty alcohol sulphate, 2.7% of coconut acid monoethanolamide, 39.0% of sodium tripolyphosphate, 4.0% of sodium silicate, 2.0% of magnesium silicate, 1.0% of carboxymethylcellulose, 0.5% of the sodium salt of ethylenediaminetetraacetic acid (EDTA) and 6.7% of water, made up to 100% with sodium sulphate.

The fabric is then washed under running water for ½ minute and dried for 20 minutes at 60° C. in a drying cabinet.

The fabric shows a strong brightening effect with good fastness to light.

The washing agent of the above composition can also contain the brightener of the formula (100) as a directly incorporated substance.

EXAMPLE 5

1 g of the brightener of the formula (100) is dissolved in 1,000 ml of dimethylformamide. 95 ml of water which contain 0.06 ml of 40% strength acetic acid are added to 6 ml of this solution. Cellulose acetate fabric weighing 3 g is added to this brightener solution, which has been warmed to 40° C. The temperature is raised to 75° to 80° C. in the course of 10 to 15 minutes and this temperature is maintained for 30 minutes. The fabric is then rinsed in running cold water for 2 minutes and susbsequently is dried at 60° C. for 20 minutes.

The fabric obtained in this way shows a strong brightening effect with good fastness to light.

EXAMPLE 6

1 g of the brightener of the formula (100) is dissolved in 1,000 ml of dimethylformamide. 95 ml of water which contain 0.06 ml of 40% strength acetic acid are added to 6 ml of this solution. Cellulose triacetate fabric weighing 3 g is added to this brightener solution, which has been warmed to 40° C. The temperature is raised to 95° to 97° C. in the course of 10 to 15 minutes and this temperature is maintained for 30 minutes. The fabric is then rinsed in running cold water for 2 minutes and subsequently is dried for 20 minutes at 60° C.

The fabric obtained in this way shows a strong brightening effect with good fastness to light.

EXAMPLE 7

In a kneader, 67 parts of polyvinyl chloride powder, 33 parts of dioctyl phthalate, 2 parts of di-n-butyl dilauryl-dioxystannate and 0.3 part of sodium pentaoctyl-tripolyphosphate are gelatinised with 0.05 part of the optical brightener of the formula (101) on mixing rolls at 160° C. for 15 minutes and the mixture is then drawn out to films. The polyvinyl chloride film produced in this way has a strong fluorescence and a brilliant white appearance in daylight.

EXAMPLE 8

1,000 parts of polyamide chips obtained in a known manner from hexamethylene adipate are mixed in a drum with 5 parts of titanium dioxide and 0.5 part of the optical brightener of the formula (101) for 10 to 16 hours. The chips treated in this way are melted in an apparatus, with the exclusion of oxygen, and the melt is stirred briefly. The melt is then spun out, under a nitrogen atmosphere of 5 atmospheres gauge, through spinnerets and stretched. The polyamide filaments obtained in this way have a high whiteness.

What is claimed is:

1. A v-triazolyl[4,5-d]-pyrimidine of the formula:

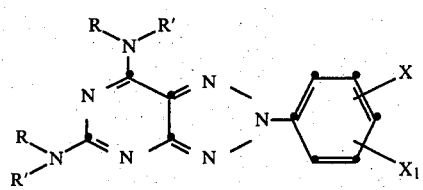

in which R and R' independently of one another are hydrogen or alkyl having 1 to 4 carbon atoms, X is —SO$_3$M, in which M is hydrogen or a salt-forming cation; alkylsulfonyl with 1 to 4 carbon atoms; or —SO$_2$NY$_1$Y$_2$, in which Y$_1$ and Y$_2$ independently of one another are hydrogen or alkyl having 1 to 4 carbon atoms and $X_1$ is hydrogen, alkyl having 1 to 4 carbon atoms, or alkoxy having 1 to 4 carbon atoms.

2. A v-triazolyl[4,5-d]-pyrimidine according to claim 1 in which R and R' independently of one another are hydrogen or methyl, X is —$SO_3M$ in which M is hydrogen or a salt-forming cation; methylsulfonyl; or —$SO_2NY_1Y_2$ in which $Y_1$ and $Y_2$ independently of one another are hydrogen or methyl and $X_1$ is hydrogen, methyl or methoxy.

3. The v-triazolyl[4,5-d]-pyrimidine according to claim 1 of the formula

4. The v-triazolyl[4,5-d]-pyrimidine according to claim 1 of the formula

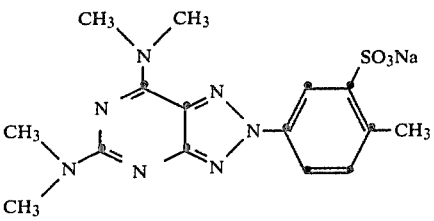

5. The v-triazolyl[4,5-d]-pyrimidine according to claim 1 of the formula

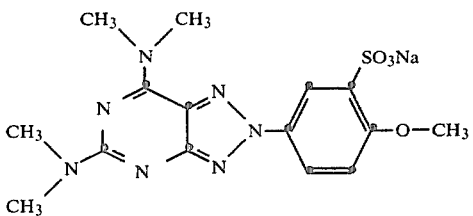

* * * * *

UNITED STATES PATENT AND TRADEMARK OFFICE
CERTIFICATE OF CORRECTION

PATENT NO. : 4,236,003
DATED : November 25, 1980
INVENTOR(S) : Ian J. Fletcher

It is certified that error appears in the above–identified patent and that said Letters Patent are hereby corrected as shown below:

Cover Page, Line 54, Title reads:

"V-TRIAZOLYL-[4,5-D]-PYRIMIDH."

Should now read:

"V-TRIAZOLYL-[4,5-D]-PYRIMIDINES".

Column 1, Title reads:

"V-TRIAZOLYL-[4,5-D]-PYRIMIDH."

Should now read:

"V-TRIAZOLYL-[4,5-D]-PYRIMIDINES".

Signed and Sealed this

Twenty-fourth Day of August 1982

|SEAL|

Attest:

GERALD J. MOSSINGHOFF

Attesting Officer     Commissioner of Patents and Trademarks